United States Patent [19]

Breard et al.

[11] Patent Number: 5,387,213
[45] Date of Patent: Feb. 7, 1995

[54] OSSEOUS SURGICAL IMPLANT PARTICULARLY FOR AN INTERVERTEBRAL STABILIZER

[75] Inventors: Francis H. Breard, Paris; Henry Graf, Lyons, both of France

[73] Assignee: Safir S.A.R.L., Montrouge, France

[21] Appl. No.: 109,701

[22] Filed: Aug. 20, 1993

Related U.S. Application Data

[63] Continuation of Ser. No. 830,936, Feb. 4, 1992, abandoned.

[30] Foreign Application Priority Data

Feb. 5, 1991 [FR] France .................. 91 01288

[51] Int. Cl.$^6$ .................... A61B 17/56; A61F 2/08; A61F 2/44
[52] U.S. Cl. .................... 606/61; 623/13; 623/17
[58] Field of Search .............. 606/61, 69, 70, 71, 606/72, 73, 74, 75, 76, 77; 623/13, 17

[56] References Cited

U.S. PATENT DOCUMENTS

| | | | |
|---|---|---|---|
| 3,997,138 | 12/1976 | Crock | 606/61 |
| 4,382,438 | 5/1983 | Jacobs | 606/61 |
| 4,790,297 | 12/1988 | Luque | 606/61 |
| 4,794,918 | 1/1989 | Wolter | 606/72 |
| 4,946,458 | 8/1990 | Harms | 606/72 |
| 4,987,892 | 1/1991 | Krag | 606/61 |
| 5,024,213 | 6/1991 | Asher | 606/61 |
| 5,084,048 | 1/1992 | Jacob | 606/61 |
| 5,092,866 | 3/1992 | Breard et al. | |
| 5,092,893 | 3/1992 | Smith | 606/61 |
| 5,108,397 | 4/1992 | White | 606/70 |

FOREIGN PATENT DOCUMENTS 0712079 1/1980 U.S.S.R. ................ 606/70

*Primary Examiner*—Michael A. Brown
*Attorney, Agent, or Firm*—Collard & Roe

[57] ABSTRACT

A surgical implant for connecting two flexible ligaments to vertebrae having an intervertebral stabilizer including an intra-osseous rod having a first end for implanting into a vertebrae. The intervertebral stabilizer also includes an extra-osseous head extending outwardly of the vertebrae. The extra-osseous head has two stepped portions, each with a peripheral surface, defining two ligament retaining zones. Each of the two ligament retaining zones has a shoulder, forming an axial ligament abutment on the sides of the ligament retaining zones closest to the first end. The extra-osseous head retains two flexible ligaments spaced from the vertebrae and each other by the shoulders.

17 Claims, 2 Drawing Sheets

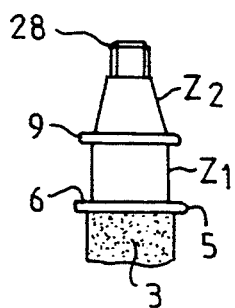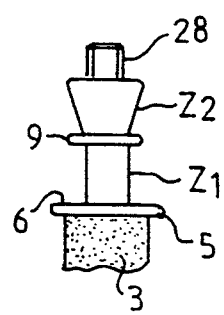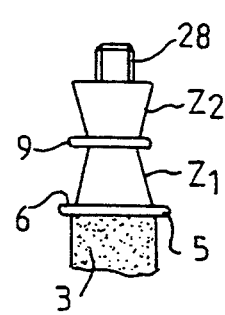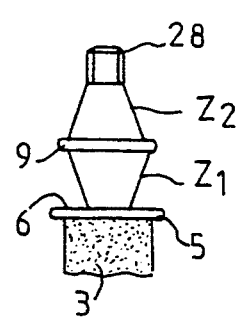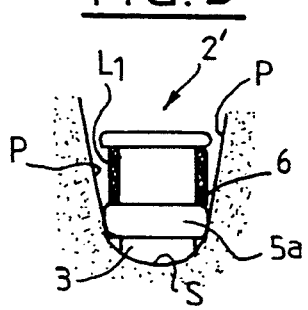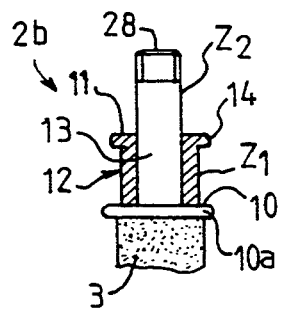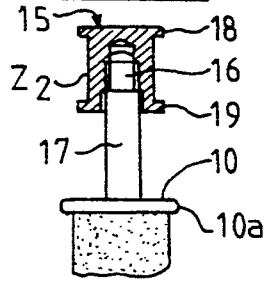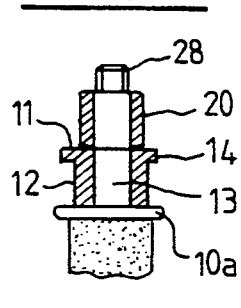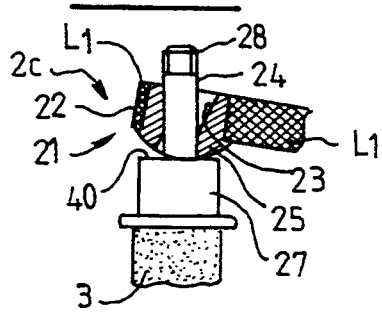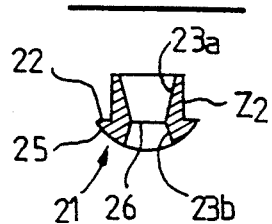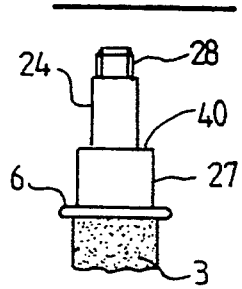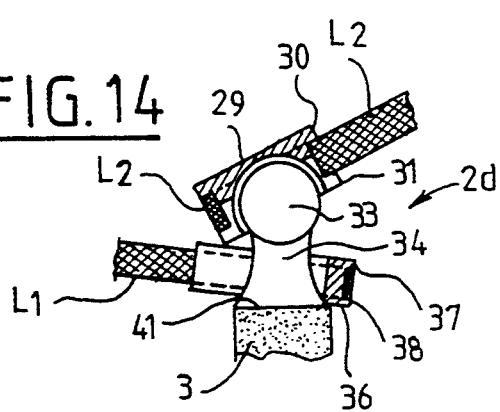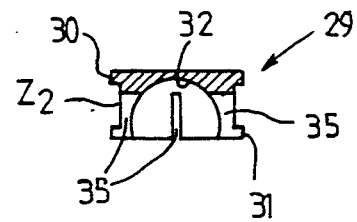

OSSEOUS SURGICAL IMPLANT PARTICULARLY FOR AN INTERVERTEBRAL STABILIZER

This is a continuation copending application Ser. No. 07/830,936 filed on Feb. 4, 1992, now abandoned.

BACKGROUND OF THE INVENTION

1. Field of the Invention

The present invention relates to a surgical implant, more particularly, for an intervertebral stabilizer, formed from an intra-osseous rod. The rod has one end implanted into the bone and another end forming an extra-osseous head for retaining at least one flexible ligament.

2. The Prior Art

In an intervertebral stabilizer of the type described in French patent application 89 01445, the implants are anchored by the intra-osseous rod in the vertebrae of the area to be treated. The extra-osseous head forms an attachment point for the ends of a flexible ligament which is thus freely retained between two successive vertebrae.

Such stabilizers have the advantage of correcting a large number of anatomical defects of the spine without impeding the natural bending and twisting movements of the trunk of the patient.

However, the repetition of these movements can, in certain cases, lead to progressive wear of the ligaments, due to excessive friction with the rough surface of the vertebrae or a second ligament mounted on the extra-osseous head of the same implant. As such wear inevitably modifies the initial tension of the ligaments or snaps the ligaments, it is necessary for the patient to undergo further surgery to repair the damaged intervertebral stabilizer.

SUMMARY OF THE INVENTION

The present invention proposes a surgical implant which overcomes the disadvantages of the prior art and provides an extra-osseous head having one or more radial shoulders defining one or more peripheral ligament retaining zones, at least at the end thereof closest to the rod.

On the extra-osseous head of the implant, the shoulder provides an axial abutment for a respective band which is confined in a retaining zone, and is protected against any wear-causing friction with the bone and/or another ligament.

Thus, according to an advantageous embodiment of the invention, the shoulder or one of the shoulders is formed in the vicinity of the implant end of the extra-osseous head, so as to keep the ligament spaced from the surface of the bone.

Preferably, the shoulder is at least partly defined by a radial collar, which limits the penetration of the bone into the intra-osseous rod and automatically defines the preferred spacing between the ligament and the bone surface.

Advantageously, the collar is extended along the rod and in the direction if the implant end thereof. When the implant is fitted in the bottom of a concavity of the bone, a long collar makes it possible to raise the extra-osseous head and move the ligament held thereon away from the walls of the concavity to prevent any lateral friction with the walls.

According to another embodiment of the invention which is a compliment or variant of the first, the shoulder or shoulders define a peripheral ligament retaining zone on a portion of the extra-osseous head which can advantageously constitute a second peripheral ligament retaining zone. Thus, the extra-osseous head can retain two ligaments in superimposed manner, while preventing any mutual friction or contact thereof which could be a source of wear.

In a simple embodiment, the shoulders of two retaining zones on a one-piece extra-osseous head are defined by a single radial collar formed thereon.

According to another feature of the invention, at least one of the portions of the extra-osseous head is formed by a threaded insert axially immobilized on a spindle integral with the rod. As a result of such an interchangeable insert, it is possible to modify the diameter of one or the other of the ligament retaining zones. In this case, the shoulder or shoulders can be defined at least partly by a radial rim or flange of the insert projecting in the vicinity of the end thereof close to the other portion of the extra-osseous head.

On a one-piece extra-osseous head or a head produced from one or more inserts, the two portions of the head on which are formed the stepped ligament retaining zones will generally be cylindrical. However, at least one of them can have a truncated cone, straight or inverted shape, in order to enable the ligament held by it to assume an inclined position with respect to the axis of the extra-osseous head in accordance with the local curvature of the spine.

In a preferred embodiment of the invention, one or both of the retaining zones is formed by the lateral surface of a threaded insert by a central opening on a spindle integral with the rod and resting on a step by a curved base formed beneath the shoulder of said retaining zone. The central opening of the insert is formed from two portions each widening towards a respective end face of the insert onto which it issues and communicating with one another by an orifice having a diameter only slightly larger than that of the spindle on which is threaded the insert.

As a result, the insert can freely pivot and thus enables the ligament which it holds to be oriented in accordance with the bending movements of the spine.

The same advantageous result is obtained in another embodiment of the invention, in which the extra-osseous head is terminated by a knee joint on which is fitted, with a freedom of pivoting, an insert, whose peripheral surface defines a respective ligament retaining zone between two shoulders formed by projecting flanges of the end faces of the insert.

The neck of the knee joint by which it is attached to a plate of the extra-osseous head could also constitute a second ligament retaining zone, preferably via a second U-shaped insert embracing the neck, the outer surface of the insert being defined by ligament stop flanges.

BRIEF DESCRIPTION OF THE DRAWINGS

Embodiments of the surgical implant according to the invention will now be described in greater detail, but in a non-limiting manner with respect to the attached drawings, wherein:

FIG. 3 is a bottom view of an alternate embodiment of the intervertebral stabilizer extending out of a bone concavity;

FIG. 4 is a side-elevational view of the extra-osseous head having a conical portion and a cylindrical portion;

FIG. 5 is a side elevational view of the extra-osseous head having a conical portion and a narrow cylindrical portion;

FIG. 6 is a side-elevational view of the extra-osseous head having two conical portions with their small ends facing each other;

FIG. 7 is a side elevational view of the extra-osseous head having two conical portions with their large ends facing each other;

FIG. 8 is a side-elevational view in part cross section with the spindle forming the second retaining zone;

FIG. 9 is a side-elevational view in part cross section with the spindle forming the first retaining zone;

FIG. 10 is a side-elevational view in part cross section having two cylindrical inserts on the spindle;

FIG. 11 is a side-elevational view in part cross section having a cylindrical portion and a pivoting portion;

FIG. 12 is a cross-sectional view of the pivoting portion from FIG. 11;

FIG. 13 is a side-elevational view of an alternate embodiment of the extra-osseous head having two cylindrical portions;

FIG. 14 is a side-elevational view of the extra-osseous head having two pivoting portions; and FIG. 15 is a cross-sectional view of one of the pivoting portions from FIG. 14.

DETAILED DESCRIPTION OF PREFERRED EMBODIMENTS

Figure 1:
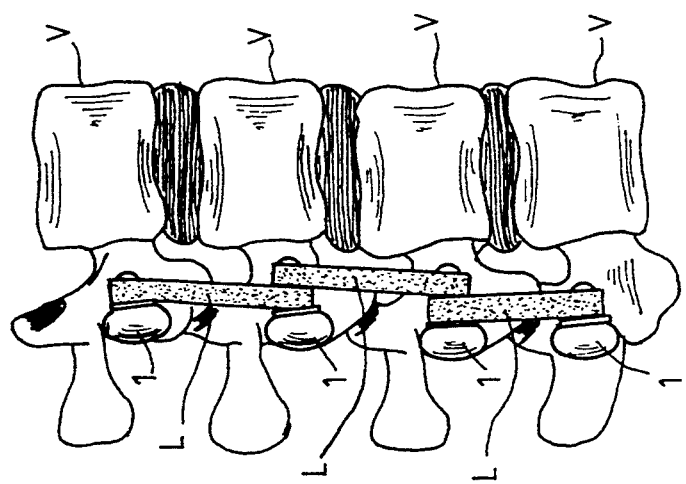
FIG. 1 is a side-elevational view of an intervertebral stabilizer according to the invention.

In general terms, an intervertebral stabilizer of the type shown in FIG. 1 comprises several flexible or artificial ligaments L, fitted in chain-like manner on metal implants 1, to the back of vertebrae V constituting the treated spine portion.

Figure 2:
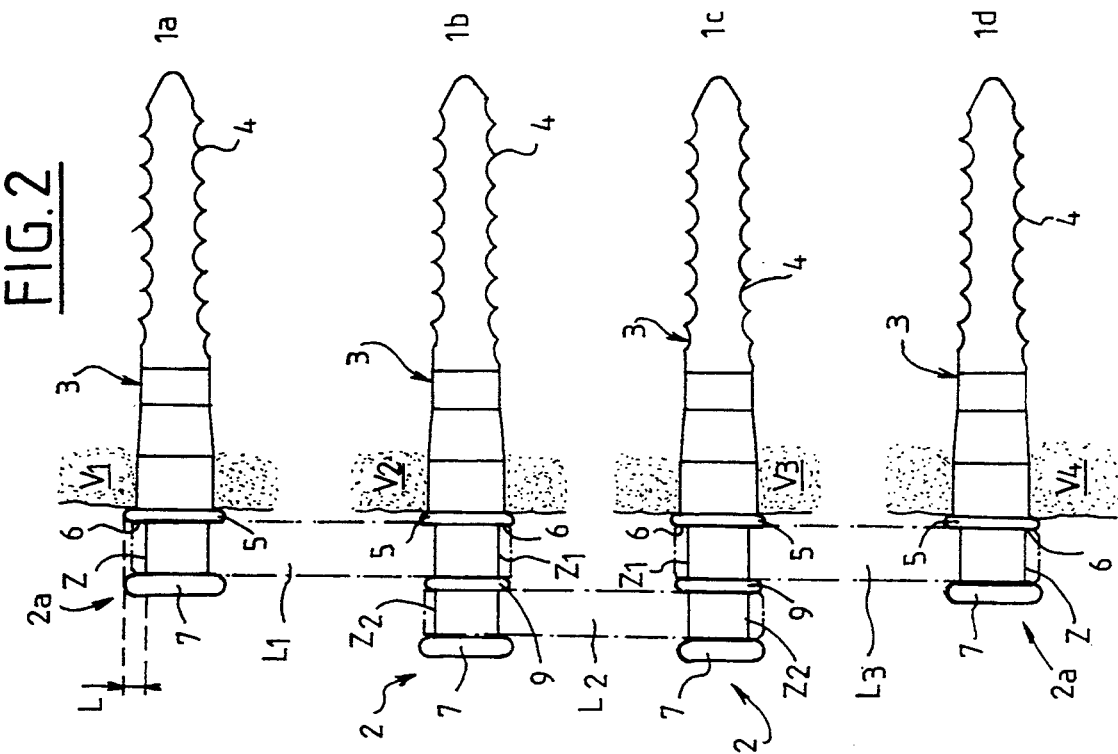
FIG. 2 is an enlarged side view of the intervertebral stabilizer shown implanted with extra-osseous heads.

The stabilizer in FIG. 2 is formed from four implants 1a, 1b, 1c, 1d according to the invention and supporting three ligaments L1, L2, L3 shown in mixed line form, on a portion or section of four vertebrae V1, V2, V3, V4. In per se known manner, each of these ligaments is a closed loop and is retained between two consecutive vertebrae by engaging extra-osseous heads 2, 2a of two implants respectively anchored in the vertebrae by an intra-osseous rod 3 having a threaded end 4.

On each implant 1a to 1d, the extra-osseous head 2 or 2a, which is cylindrical and has a circular cross section, is mounted on intra-osseous rod 3 beyond a radial collar 5. Collar 5 defines an annular shoulder 6 facing the free end of head 2 or 2a, which has a radially overdimensioned, detachable circular cap or cover 7. In the radial direction, shoulder 6 has a width W between 1 and 3 times the thickness of a ligament, which is formed with a flat strand of synthetic threads.

During the anchoring of implant 1 in a vertebra, intra-osseous rod 3 penetrates the vertebra until collar 5 is in contact with a bone surface S. Ligaments L1, L2 or L3 which are mounted on head 2 or 2a, are maintained an axial distance from the bone by shoulder 6 which forms an abutment and thus prevents any friction which is a source of wear and breaking.

As shown in FIG. 3, the height of collar 5a can also be increased along rod 3 in order to raise shoulder 6 relative to bone surface S. When implant head 2' is in the bottom of a concavity of the vertebra, raised shoulder 6 keeps ligament L1 protected against any lateral friction with the concavity walls P.

As can be seen in FIG. 2, the end implants 1a and 1d of the stabilizer, shoulder 6 and cap 7 define, on the cylindrical surface of head 2a, a single retaining zone Z having a height substantially equal to the width of a ligament for the attachment of the first or third ligaments L1 or L3.

The cylindrical surface of elongated head 2 of each of intermediate implants 1b and 1c retains one above the other and in accordance with crossed positions, two ligaments. Head 2 is subdivided between shoulder 6 and cap 7 into two stepped retaining zones Z1, Z2 of the same height as retaining zone Z of implants 1a and 1d and separated by a radial collar 9 formed mid-way along head 2. Each of the two faces of collar 9 forms, for the ligament attached to a respective retaining zone Z1 or Z2 of each head 2, an abutment maintaining it spaced from the ligament bearing on the other retaining zone Z2 or Z1 and thus preventing any mutual friction, which could lead to a breaking of one or other of the ligaments.

FIGS. 4 to 7 show that at least one of the retaining zones Z1 and Z2, separated by collar 9, can have a truncated cone shape so that, if need be, it enables the ligament which it supports to assume a certain inclination with respect to the axis of the head. In FIGS. 4 and 5, only the upper zone Z2 is formed on a truncated cone placed in a straight or inverted position on the lower cylindrical portion of the head 2 defining the second retaining zone Z1. In FIGS. 6 and 7, both retaining zones Z1 and Z2 are formed with identical truncated cones joined by their small bases or large bases, respectively.

FIG. 8 shows an extra-osseous implant head 2b formed from a cylindrical insert 12 having a central opening and threaded on a spindle 13 projecting beyond a plate 10 of the head on which insert 12 rests. Plate 10 is bordered by a collar 10a fulfilling the same function as collar 5 of the implant heads of FIG. 2. In the thus formed head, lower retaining zone Z1 is defined on the lateral cylindrical surface of insert 12 between an upper radial flange 14 of the latter and the shoulder defined by plate 10. Upper retaining zone Z2 is formed on the free portion of spindle 13 beyond a step 11 forming the upper face of insert 12.

FIG. 9 shows a variation from FIG. 8 in which an insert 15 is screwed by a central tap onto a thread 16 of the free end of a spindle 17 defining the lower retaining zone Z1 between the lower face 15a of insert 15 and plate 10, the upper retaining zone Z2 being formed on insert 15 between two radial flange 18, 19 constituting the ligament stop shoulders.

FIG. 10 illustrates a further embodiment of FIG. 8, according to which a second insert 20, which is threaded on the upper half of spindle 13, bears on step 11 of first insert 12. Thus, if need be, it is possible to increase the diameter of upper retaining zone Z2 initially defined by spindle 13.

In the embodiment of the invention shown in FIG. 11, implant head 2c is produced from a cylindrical insert 21, having a central opening 23 and threaded onto a spindle 24 which projects beyond a step 40. Step 40 is substantially formed at mid-height of a fixed part of the head, as can be seen in FIG. 13. However, here, insert 21 rests on the step 40 with a curved base 25 in spherical form and which is located below a shoulder 22 facing the free end of the head. Moreover, as can be seen in FIG. 12, central opening 23 tapers from the upper face of insert 21, in the form of a first truncated cone-shaped part 23a. Cone-shaped part 23a extends substantially to the height of shoulder 22 where, having a diameter which is only just larger than that of spindle 24, it again widens in the form of a second truncated cone-shaped portion 23b issuing onto the curved lower face of the base 25.

Spherical base 25 bears on step 40 providing insert 21 the freedom to pivot around the center of the orifice 26 joining the two truncated cone-shaped portions 23a, 23b of its central opening 23. Thus, ligament L1 engaged around the upper retaining zone Z2 of head 2c, defined on the lateral surface of insert 21 and stopped by shoulder 22 can be freely oriented as a function of the bending movements of the spine. The large diameter, lower cylindrical portion 27 of the head 2c can, if need be, be given a radial flange around step 40 in order to define a second retaining zone.

In FIGS. 11 and 13 on the one hand and FIGS. 4 to 8 and 10 on the other, it is possible to see on the free end of the extra-osseous head or spindle 13, a threaded portion 28, onto which is screwed the detachable cap 7 described with reference to FIG. 2.

FIG. 14 shows another embodiment of implant head 2d in which an insert 29, whose cylindrical surface forms a ligament retaining zone Z2 between the upper 30 and lower 31 radial flanges. An inner spherical cavity 32 is connected to a knee joint 33 formed at the end of a neck 34 projecting from a plate 41 of the head. Insert 29 made from a titanium alloy having shape memory is fitted onto knee joint 33 by means of four axial slots 35 made in the wall of cavity 32 at 90° from one another, as shown in FIG. 15. A second U-shaped insert 36, whose outer surface is defined by upper peripheral flange 37 and lower peripheral flange 38 is also connected to neck 34 of knee joint 33.

In this embodiment of the invention, each of the two inserts 29 and 36 can receive, between their flanges 30, 31 or 37, 38 the end of a respective ligament L1 or L2. Inserts 29 and 36 can pivot freely, the first around knee joint 33 and the second around neck 34, they enable two ligaments to be oriented at random as a function of bending movements of the spine without coming into mutual contact, as can best be seen in FIG. 14.

We claim:

1. A surgical implant for connecting two supple ligaments to a vertebra, comprising:
   an intra-osseous rod having a first end for implanting into a vertebra and an extra-osseous head extending outwardly of the vertebra,
   said extra-osseous head having two stepped portions with peripheral surfaces defining two ligament retaining zones with sides,
   each of said two ligament retaining zones having a shoulder forming an axial ligament abutment on the sides of said two ligament retaining zones closest to said first end,
   two supple ligaments, each supple ligament having an initial tension and being retained between two different consecutive vertebrae,
   one of said ligament retaining zones retains one of said supple ligaments axially spaced from the vertebra by the corresponding shoulder,
   the other of said ligament retaining zones retains the other of said supple ligaments axially spaced from the one supple ligament by the corresponding shoulder, and
   wherein said shoulders prevent progressive wear of said supple ligaments due to friction with the vertebrae and each other, so that the initial tension of the ligaments on the extra-osseous head is maintained and anatomical defects are corrected without impeding natural movement of the vertebrae.

2. The surgical implant according to claim 1, additionally including a junction in the region where said intra-osseous rod and said extra-osseous head meet, and wherein one of said shoulders is formed as a first radial collar located at the junction and extending a predetermined distance along said intra-osseous rod in the direction of the first end.

3. The surgical implant according to claim 2, wherein each of said two ligament retaining zones has a shoulder on the sides of said two ligament retaining zones facing the other of said ligament retaining zones.

4. The surgical implant according to claim 3, wherein said extra-osseous head is formed as one piece and includes a second radial collar located between said two ligament retaining zones, said collar having two faces opposite each other, wherein said two faces form the two shoulders located on the sides of each ligament retaining zones facing the other ligament retaining zone.

5. The surgical implant according to claim 1, wherein each of said two ligament retaining zones has a shoulder on the sides of each ligament retaining zones facing the other of said ligament retaining zones.

6. The surgical implant according to claim 5, wherein said extra-osseous head is formed as one piece and includes a radial collar located between said two ligament retaining zones, said collar having two faces opposite each other, wherein said two faces form the two shoulders located on the sides of each ligament retaining zones facing the other ligament retaining zone.

7. The surgical implant according to claim 1, wherein at least one of said two ligament retaining zones is shaped as a truncated cone.

8. A surgical implant for connecting two supple ligaments to a vertebra, comprising:
   an intra-osseous rod having a first end for implanting into a vertebra and an extra-osseous head extending outwardly of the vertebra, said extra-osseous head having two stepped portions with peripheral surfaces defining two ligament retaining zones with sides, each of said two ligament retaining zones having a shoulder forming an axial ligament abutment on the sides of said two ligament retaining zones closest to said first end, so that said extra-osseous head retains two supple ligaments spaced from the vertebrae and each other by said shoulders,
   wherein said extra-osseous head includes a spindle integrally formed with said intra-osseous rod, and wherein at least one of said two ligament retaining zones is formed by a threaded insert securable to said spindle.

9. A surgical implant for connecting two supple ligaments to a vertebra, comprising:
   an intra-osseous rod having a first end for implanting into a vertebra and an extra-osseous head extending outwardly of the vertebra, said extra-osseous head having two stepped portions with peripheral surfaces defining two ligament retaining zones with sides, each of said two ligament retaining zones having a shoulder forming an axial ligament abutment on the sides of said two ligament retaining zones closest to said first end, so that said extra-osseous head retains two supple ligaments spaced from the vertebra and each other by said shoulders, wherein said extra-osseous head includes a spindle integrally formed with said intra-osseous rod and having a step, one of said ligament retaining zones being formed as an insert having two sides and a central opening for receiving said spindle, said insert having a curved base formed on one of the sides of said shoulder opposite said ligament retaining zone, said curved base resting on said step, the central opening extending from one side of said insert to the other and being formed from two portions, said insert having an orifice located within the central opening having a diameter slightly larger than said spindle, said two portions communicating with the orifice and said two sides, and having widths that increase from the width of the orifice to larger widths at said two sides.

10. A surgical implant for connecting two supple ligaments to a vertebra, comprising:

an intra-osseous rod having a first end for implanting into a vertebra and an extra-osseous head extending outwardly of the vertebra, said extra-osseous head having two stepped portions with peripheral surfaces defining two ligament retaining zones with sides, each of said two ligament retaining zones having a shoulder forming an axial ligament abutment on the sides of said two ligament retaining zones closest to said first end, so that said extra-osseous head retains two supple ligaments spaced from the vertebra and each other by said shoulders, a junction in the region where said intra-osseous rod and said extra-osseous head meet, and wherein one of said shoulders is formed as a first radial collar located at the junction and extending a predetermined distance along said intra-osseous rod in the direction of the first end, wherein said extra-osseous head includes a spindle integrally formed with said intra-osseous rod and having a step, one of said ligament retaining zones being formed as an insert having two sides and a central opening for receiving said spindle, said insert having a curved base formed on one of the sides of said shoulder opposite said ligament retaining zone, said curved base resting on said step, the central opening extending from one side of said insert to the other and being formed from two portions, said insert having an orifice located within the central opening having a diameter slightly larger than said spindle, said two portions communicating with the orifice and said two sides, and having widths that increase from the width of the orifice to larger widths at said two sides.

11. A surgical implant for connecting two supple ligaments to a vertebra, comprising:

an intra-osseous rod having a first end for implanting into a vertebra and an extra-osseous head extending outwardly of the vertebra, said extra-osseous head having two stepped portions with peripheral surfaces defining two ligament retaining zones with sides, each of said two ligament retaining zones having a shoulder forming an axial ligament abutment on the sides of said two ligament retaining zones closest to said first end, so that said extra-osseous head retains two supple ligaments spaced from the vertebra and each other by said shoulders, a junction in the region where said intra-osseous rod and said extra-osseous head meet, and wherein one of said shoulders is formed as a first radial collar located at the junction and extending a predetermined distance along said intra-osseous rod in the direction of the first end, wherein each of said two ligament retaining zones has a shoulder on the sides of said two ligament retaining zones facing the other of said ligament retaining zones, wherein said extra-osseous head includes a spindle integrally formed with said intra-osseous rod and having a step, one of said ligament retaining zones being formed as an insert having two sides and a central opening for receiving said spindle, said insert having a curved base formed on one of the sides of said shoulder opposite said ligament retaining zone, said curved base resting on said step, the central opening extending from one side of said insert to the other and being formed from two portions, said insert having an orifice located within the central opening having a diameter slightly larger than said spindle, said two portions communicating with the orifice and said two sides, and having widths that increase from the width of the orifice to larger widths at said two sides.

12. A surgical implant for connecting two supple ligaments to a vertebra, comprising:

an intra-osseous rod having a first end for implanting into a vertebra and an extra-osseous head extending outwardly of the vertebra, said extra-osseous head having two stepped portions with peripheral surfaces defining two ligament retaining zones with sides, each of said two ligament retaining zones having a shoulder forming an axial ligament abutment on the sides of said two ligament retaining zones closest to said first end, so that said extra-osseous head retains two supple ligaments spaced from the vertebra and each other by said shoulders, wherein each of said two ligament retaining zones has a shoulder on the sides of each ligament retaining zones facing the other of said ligament retaining zones, wherein said extra-osseous head includes a spindle integrally formed with said intra-osseous rod and having a step, one of said ligament retaining zones being formed as an insert having two sides and a central opening for receiving said spindle, said insert having a curved base formed on one of the sides of said shoulder opposite said ligament retaining zone, said curved base resting on said step, the central opening extending from one side of said insert to the other and being formed from two portions, said insert having an orifice located within the central opening having a diameter slightly larger than said spindle, said two portions communicating with the orifice and said two sides, and having widths that increase from the width of the orifice to larger widths at said two sides.

13. A surgical implant for connecting two supple ligaments to a vertebra, comprising:

an intra-osseous rod having a first end for implanting into a vertebra and an extra-osseous head extending outwardly of the vertebra, said extra-osseous head having two stepped portions with peripheral surfaces defining two ligament retaining zones with sides, each of said two ligament retaining zones having a shoulder forming an axial ligament abutment on the sides of said two ligament retaining zones closest to said first end, so that said extra-osseous head retains two supple ligaments spaced from the vertebra and each other by said shoulders, wherein said extra-osseous head includes a neck integrally formed with said intra-osseous rod and a knee joint, an insert with projecting flanges and end faces pivotally coupled to said knee joint and having a peripheral surface including two shoulders formed by said projecting flanges of the end faces, said peripheral surface defining a ligament retaining zone, and a U-shaped insert pivotally connected to said neck and having an outer peripheral surface and two peripheral flanges, forming a second ligament retaining zone.

14. A surgical implant for connecting two supple ligaments to a vertebra, comprising:

an intra-osseous rod having a first end for implanting into a vertebra and an extra-osseous head extending outwardly of the vertebra, said extra-osseous head having two stepped portions with peripheral surfaces defining two ligament retaining zones with sides, each of said two ligament retaining zones having a shoulder forming an axial ligament abutment on the sides of said two ligament retaining zones closest to said first end, so that said extra-osseous head retains two supple ligaments spaced from the vertebra and each other by said shoulders, a junction in the region where said intra-osseous rod and said extra-osseous head meet, and wherein one of said shoulders is formed as a first radial collar located at the junction and extending a predetermined distance along said intra-osseous rod in the direction of the first end, wherein said extra-osseous head includes a neck integrally formed with said intra-osseous rod and a knee joint, an insert with projecting flanges and end faces pivotally coupled to said knee joint and having a peripheral surface including two shoulders formed by said projecting flanges of the end faces, said peripheral surface defining a ligament retaining zone, and a U-shaped insert pivotally connected to said neck and having an outer peripheral surface and two peripheral flanges, forming a second ligament retaining zone.

15. A surgical implant for connecting two supple ligaments to a vertebra, comprising:

an intra-osseous rod having a first end for implanting into a vertebra and an extra-osseous head extending outwardly of the vertebra, said extra-osseous head having two stepped portions with peripheral surfaces defining two ligament retaining zones with sides, each of said two ligament retaining zones having a shoulder forming an axial ligament abutment on the sides of said two ligament retaining zones closest to said first end, so that said extra-osseous head retains two supple ligaments spaced from the vertebra and each other by said shoulders, a junction in the region where said intra-osseous rod and said extra-osseous head meet, and wherein one of said shoulders is formed as a first radial collar located at the junction and extending a predetermined distance along said intra-osseous rod in the direction of the first end, wherein each of said two ligament retaining zones has a shoulder on the sides of said two ligament retaining zones facing the other of said ligament retaining zones, wherein said extra-osseous head includes a neck integrally formed with said intra-osseous rod and a knee joint, an insert with projecting flanges and end faces pivotally coupled to said knee joint and having a peripheral surface including two shoulders formed by said projecting flanges of the end faces, said peripheral surface defining a ligament retaining zone, and a U-shaped insert pivotally connected to said neck and having an outer peripheral surface and two peripheral flanges, forming a second ligament retaining zone.

16. A surgical implant for connecting two supple ligaments to a vertebra, comprising:

an intra-osseous rod having a first end for implanting into a vertebra and an extra-osseous head extending outwardly of the vertebra, said extra-osseous head having two stepped portions with peripheral surfaces defining two ligament retaining zones with sides, each of said two ligament retaining zones having a shoulder forming an axial ligament abutment on the sides of said two ligament retaining zones closest to said first end, so that said extra-osseous head retains two supple ligaments spaced from the vertebra and each other by said shoulders, wherein each of said two ligament retaining zones has a shoulder on the sides of each ligament retaining zones facing the other of said ligament retaining zones, wherein said extra-osseous head includes a neck integrally formed with said intra-osseous rod and a knee joint, an insert with projecting flanges and end faces pivotally coupled to said knee joint and having a peripheral surface including two shoulders formed by said projecting flanges of the end faces, said peripheral surface defining a ligament retaining zone, and a U-shaped insert pivotally connected to said neck and having an outer peripheral surface and two peripheral flanges, forming a second ligament retaining zone.

17. A surgical implant for connecting two supple ligaments to a vertebra comprising:

an intra-osseous rod having a first end for implanting into a vertebra and an extra-osseous head extending outwardly of the vertebra, said extra-osseous head having two stepped portions with peripheral surfaces defining two ligament retaining zones with sides, each of said two ligament retaining zones having a shoulder forming an axial ligament abutment on the sides of said two ligament retaining zones closest to said first end, so that one of said ligament retaining zones retains one supple ligament axially spaced from the vertebra by one of said shoulders, and the other of said ligament retaining zones retains the other supple ligament axially spaced from the one ligament by the other of said shoulders, wherein each of said two ligament retaining zones has a shoulder on the sides of each ligament retaining zones facing the other of said ligament retaining zones, wherein said extra-osseous head is formed as one piece and includes a radial collar located between said two ligament retaining zones, said collar having two faces opposite each other, wherein said two faces from the two shoulders located on the sides of each ligament retaining zones facing the other ligament retaining zone, and a threaded insert with two ends, said shoulders being formed on at least one of the ends of said insert, and including a radial flange.

* * * * *